(12) United States Patent
Mueller et al.

(10) Patent No.: US 11,918,325 B2
(45) Date of Patent: Mar. 5, 2024

(54) PULSE WAVE VELOCITY MEASUREMENT SYSTEM

(71) Applicant: KONINKLIJKE PHILIPS N.V., Eindhoven (NL)

(72) Inventors: Manfred Mueller, Eindhoven (NL); Arjen Van Der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 334 days.

(21) Appl. No.: 17/288,101

(22) PCT Filed: Oct. 25, 2019

(86) PCT No.: PCT/EP2019/079253
§ 371 (c)(1),
(2) Date: Apr. 23, 2021

(87) PCT Pub. No.: WO2020/084140
PCT Pub. Date: Apr. 30, 2020

(65) Prior Publication Data
US 2021/0378528 A1 Dec. 9, 2021

(30) Foreign Application Priority Data

Oct. 26, 2018 (EP) .................................. 18202912
Mar. 28, 2019 (EP) .................................. 19165687

(51) Int. Cl.
| | |
|---|---|
| *A61B 5/021* | (2006.01) |
| *A61B 5/02* | (2006.01) |
| *A61B 5/0215* | (2006.01) |
| *A61B 5/026* | (2006.01) |
| *A61B 5/107* | (2006.01) |
| *A61B 34/20* | (2016.01) |
| *A61B 90/00* | (2016.01) |

(52) U.S. Cl.
CPC ...... *A61B 5/02125* (2013.01); *A61B 5/02007* (2013.01); *A61B 5/02158* (2013.01);
(Continued)

(58) Field of Classification Search
CPC ............ A61B 5/02125; A61B 5/02007; A61B 5/02158; A61B 5/026; A61B 5/1076;
(Continued)

(56) References Cited

U.S. PATENT DOCUMENTS 5,241,964 A * 9/1993 McQuilkin ........ A61B 5/02125
600/485
6,053,873 A 4/2000 Govari
(Continued)

FOREIGN PATENT DOCUMENTS

WO 199934724 A2 7/1999
WO 2017198490 A1 11/2017
(Continued)

OTHER PUBLICATIONS

International Search Report and Written Opinion of PCT/EP2019079253, dated Jan. 23, 2020.
(Continued)

*Primary Examiner* — Rochelle D Turchen

(57) ABSTRACT

A system and method is disclosed for measurement of pulse wave velocity of a vessel. An intravascular device comprises a first and a second marker provided at different locations along the length of the intravascular device of which positions are localizable by a tracking apparatus. The intravascular device provides plurality of measurements along the length of the vessel, while the intravascular device is moved from a first position to a second position, corresponding to a first and a second time. At the second time the position of the first marker in the vessel corresponds to the position of the second marker at the first time. The pulse wave velocity value of the vessel is ascertained based on measurements associated for the first time and the second time from the (Continued)

plurality of measurements and based on the distance between the locations of the two markers along the length of the intravascular device.

15 Claims, 5 Drawing Sheets

(52) U.S. Cl.
CPC ............ *A61B 5/026* (2013.01); *A61B 5/1076* (2013.01); *A61B 34/20* (2016.02); *A61B 90/39* (2016.02); *A61B 2034/2051* (2016.02); *A61B 2034/2063* (2016.02); *A61B 2090/3966* (2016.02); *A61B 2090/3975* (2016.02)

(58) Field of Classification Search
CPC . A61B 34/20; A61B 90/39; A61B 2034/2051; A61B 2034/2063; A61B 2090/3966; A61B 2090/3975; A61B 5/7207; A61B 8/5223; A61B 6/504; A61B 8/0841; A61B 8/0858; A61B 2562/04; A61B 2562/043; A61B 5/02108; A61B 5/0215; A61B 5/065; A61B 5/1072; A61B 5/201; A61B 8/0891; A61B 18/00; A61B 8/04; A61B 8/06; A61B 8/12; A61B 6/12; A61B 90/00
See application file for complete search history.

(56) References Cited

U.S. PATENT DOCUMENTS

| | | |
|---|---|---|
| 8,798,712 B2 | 8/2014 | Gopinathan |
| 2006/0058653 A1* | 3/2006 | Sathyanarayana ....... A61B 8/06 |
| | | 600/437 |
| 2011/0275925 A1* | 11/2011 | Leichner ................ A61B 5/287 |
| | | 600/407 |
| 2012/0215117 A1* | 8/2012 | Karst ................. A61N 1/36585 |
| | | 600/486 |
| 2012/0215275 A1* | 8/2012 | Wenzel ............. A61B 5/02125 |
| | | 607/19 |
| 2018/0360417 A1 | 12/2018 | Henneken |
| 2019/0046047 A1 | 2/2019 | Haase |
| 2019/0082978 A1 | 3/2019 | Van Der Horst |
| 2020/0069196 A1* | 3/2020 | Hettrick ................ A61B 5/4848 |
| 2020/0178816 A1* | 6/2020 | Lantelm ................ A61B 5/7235 |

FOREIGN PATENT DOCUMENTS

| | | |
|---|---|---|
| WO | 2017198800 A1 | 11/2017 |
| WO | 2017198867 A1 | 11/2017 |
| WO | 2017198871 A1 | 11/2017 |

OTHER PUBLICATIONS

Harbaoui, Brahim et al "Development of Coronary Pulse Wave Velocity: New Pathophysiological Insight into Cronary Artery Disease", American Heart Association, Oct. 2018.

Millasseau, Sandrine C. et al "Evaluation of Carotid-Femoral Pulse Wave Velocity Influence of Timing Algorithm and Heart Rate", Hypertension, Dec. 2005.

Davies, Justin E. et al "Use of Simultaneous Pressure and Velocity Measurements to Estimate Arterial Wave Speed at a single Site in humans", Americn Journal Physiology Heart Circ. Physiolo. vol. 290, 2006.

Khir, A.W. et al "Determination of Wave Speed and Wave Separation in the Artieries", Journal of Biomechanics, vol. 34, 2001, pp. 1145-1155.

* cited by examiner

PULSE WAVE VELOCITY MEASUREMENT SYSTEM

CROSS-REFERENCE TO PRIOR APPLICATIONS

This application is the U.S. National Phase application under 35 U.S.C. § 371 of International Application No. PCT/EP2019/079253, filed on Oct. 25, 2019, which claims the benefit of European Patent Application No. 18202912.4, filed on Oct. 26, 2018 and European Patent Application No. 19165687.5, filed on Mar. 28, 2019. These applications are hereby incorporated by reference herein.

FIELD OF THE INVENTION

The present invention relates to a medical system and method of measuring pulse wave velocity of a vessel with the medical system.

BACKGROUND OF THE INVENTION

Pulse wave velocity (PWV) measurements are a well-established way to measure the compliance of major blood vessels. Aortic and cardiac PWV are used to evaluate the risk of cardiovascular events while the renal PWV may help in patent stratification for renal denervation.
There are two mainstream ways of measuring PWV:
  a) By measuring flow and pressure at (approximately) the same location and deriving PWV from the relationship between the change in pressure and the change in flow velocity (e.g. Khir et. al., Determination of wave speed and wave separation in the arteries, Journal of Biomechanics 34, 2001, 1145-1155; and Davies et. al., Use of simultaneous pressure and velocity measurements to estimate arterial wave speed at a single site in humans, Am J Physiol Heart Circ Physiol 290: H878-H885, 2006);
  b) by timing the rise of a wave or pressure pulse over a known distance (Millasseau et. al., Evaluation of Carotid-Femoral Pulse Wave Velocity: Influence of Timing Algorithm and Heart Rate, Hypertension. 2005; 45:222-226; and Harbaoui et. al., Development of Coronary Pulse Wave Velocity: New Pathophysiological Insight Into Coronary Artery Disease, Journal of the American Heart Association 2017; 6:e004981). Both methods have their advantages and disadvantages. Measuring PWV via the pressure-flow-relationship typically requires an intravascular flow-pressure-wire. Timing the pressure or flow wave is technically less demanding but works best for long blood vessels like the aorta, where delay times are long and comparatively easy to measure. However, for applications like patient stratification for renal denervation, it is necessary to measure PWV in blood vessels only a few cm long, such as the renal artery.

SUMMARY OF THE INVENTION

It is an object of the invention to provide a medical system for measuring PWV in blood vessels with improved accuracy and reproducibility.
The system comprises an intravascular guidewire/catheter with a single pressure or flow sensor and a processing unit configured to derive a delay time between an electrocardiogram (ECG) signal or additional pressure signal and the pressure/flow signal measured by the sensor whereby the intravascular device comprises special markings near the sensor that allow an imaging or tracking modality (angiography, ultrasound, electro-magnetic tracking) to determine a pullback distance with a high degree of accuracy.

In an embodiment, the system for measuring PWV in blood vessels comprises an intravascular guidewire/catheter with a single pressure or flow sensor and a processing unit to derive a delay time between an ECG or additional pressure signal and the pressure/flow signal measured by the sensor whereby the intravascular device comprises at least two markings at and proximally from the sensor, wherein the at least two markings form a ruler that allows an imaging or tracking modality (angiography, ultrasound, electro-magnetic tracking) to determine a pullback distance with a high degree of accuracy independently of the alignment between imaging plane and sensor.

In an aspect of the invention a method of measurement of pulse wave velocity of a vessel is presented, wherein the method comprises:
  receiving plurality of measurements along the length of the vessel from an intravascular device, the intravascular device comprising two markers provided at different locations along the length of the intravascular device of which positions are localizable by a tracking apparatus;
  receiving position information of the two markers from the tracking apparatus;
  associating for a first time a measurement of the plurality of measurements with the positions of the markers, wherein the first marker is in a first position and the second marker is in a second position,
  detecting upon movement of the intravascular device from the position information when the first marker is reaching the second position and associating a second time;
  ascertaining the pulse wave velocity value of the vessel based on measurements associated for the first time and the second time from the plurality of measurements and based on the distance between the locations of the two markers along the length of the intravascular device.

Additional aspects and advantages of the invention will become more apparent from the following detailed description, which may be best understood with reference to and in conjunction with the accompanying drawings.

DETAILED DESCRIPTION OF EMBODIMENTS

Pulse wave velocity can be determined by measuring the time delay $\Delta t$ of a pressure or flow velocity wave when travelling a distance $\Delta x$ as:

$$PWV = \frac{\Delta t}{\Delta x} \qquad \text{Eq. 1}$$

Figure 1:
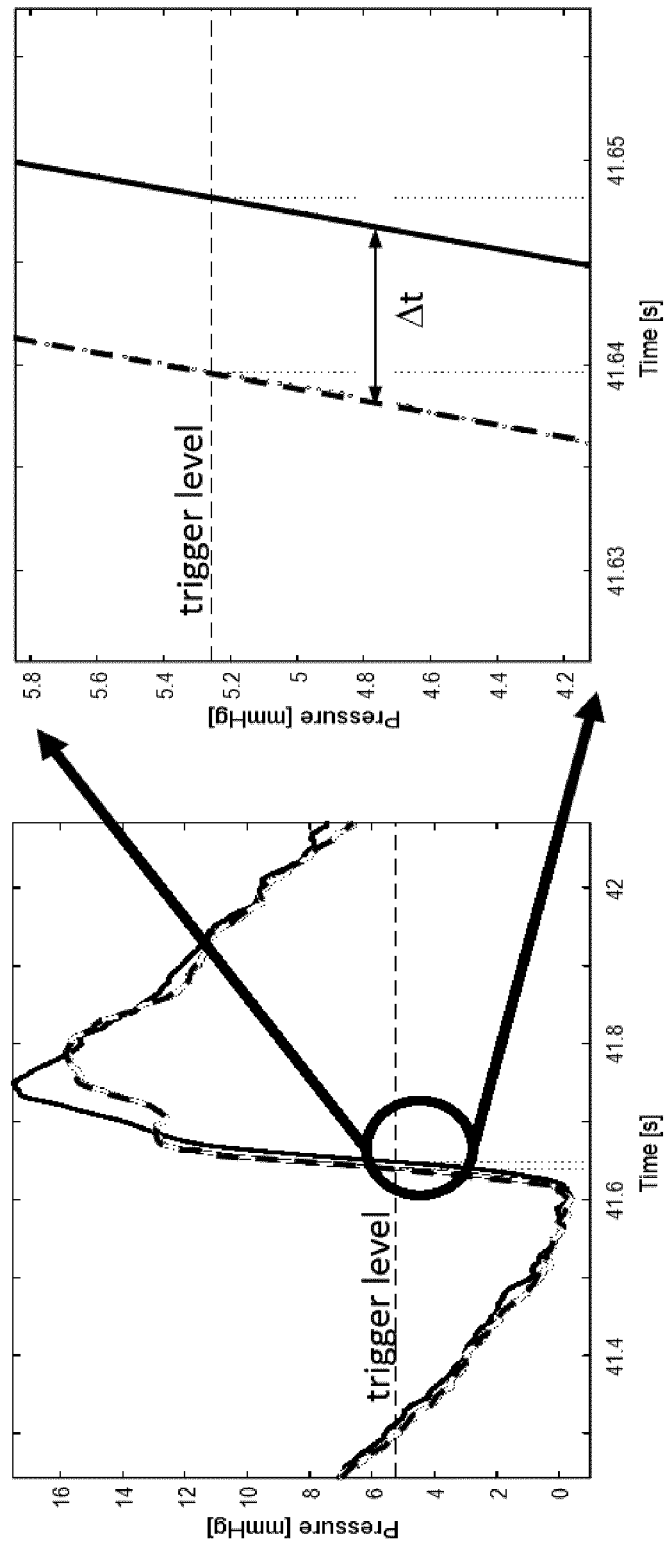
FIG. 1 shows exemplarily typical pressure signals (pressure versus time over one heartbeat).

It is therefore possible to measure PWV with two (pressure or flow) sensors located at a known distance from each other. FIG. 1 shows how such a double measurement can be used to determine Δt. However, this requires an intravascular device with two pressure sensors. Such a device is currently not commercially available for human use. It would also probably cost twice as much as a standard pressure or flow wire with a single sensor and the need to comprise connective cables for two sensors would likely compromise the mechanical properties of the device.

It is also possible to measure the time delay Δt of a pressure or flow velocity wave with a single sensor (pressure or flow), by pulling back the sensor along the vessel to measure at different locations sequentially. In this case one needs a reference signal from which to time each pulse. Typically, one uses the ECG signal or the signal from a central pressure sensor. The method is described in detail in Harbaoui et. al. This method is usually advantageous because it only requires a single pressure or flow sensor.

However, using a single sensor can significantly decrease accuracy, especially for measurements in short arteries. This is because the need to move the sensor adds inaccuracy in the distance Δx between measurement locations, while for a two-sensor probe the distance between sensors is mechanically fixed with very little error. For measurements in long arteries, the relative error in distance can typically be neglected, but in arteries that are only a few centimeters long, the error quickly becomes unacceptably large. For example, if one measures PWV in the aorta over a distance of Δx=40 cm then an error of ±1 mm in the placement of each sensor only causes a relative error of 0.5%. But if one measures in a short artery like the renal artery where the distance between measurement points is only Δx=2 mm, then the same absolute error of ±1 mm in the placement of each sensor already causes a relative error of 10%.

This problem is made worse because it is difficult to measure the location of the sensor in the vessel with an accuracy of ±1 mm or better. Harbaoui et. al. try to overcome the issue by measuring the displacement of the external part of the device during pullback. This is unfortunately not accurate enough for measuring PWV in short arteries. The reason for this is that any intravascular device (guide wire, catheter, etc.) when advanced deeper into a vessel will follow the vessel wall and bunch up. Subsequently, during pullback the shaft of the device will straighten. Also during pullback, parts of the device can catch or snag at the vessel walls leading to a non-smooth movement of the device tip. As a consequence, the displacement of the sensor integrated at the tip portion of the device will typically be less than the displacement of the external shaft during pullback. This uncertainty scales with the total length of the device inside the patient and is most problematic for measurement of PWV in short arteries. For example, if a device has 1 m of its length inside the patient, and if there is 0.5% deviation between the displacement of the distal tip and the displacement of the external shaft, then there will be a relative error of 25% when measuring Δx inside a 2 cm long renal artery, but the error will only be 2.5% when measuring Δx inside a 20 cm long artery.

Alternatively, one could try to determine the sensor displacement by using imaging. Angiography is typically used to navigate a sensor wire or catheter because the physician can observe the movement of the device and sensor inside the blood vessel directly. Unfortunately, the movement seen on a two-dimensional (2D) angiogram is only the projection of the actual three-dimensional (3D) movement onto a 2D plane. If the C-arm is not perfectly aligned with the blood vessel and the device, or if the blood vessel is not perfectly straight, this can introduce significant inaccuracies.

For the reasons given above, PWV measurement with a single sensor (and manual pullback) is currently not reliable in short arteries. To increase the accuracy of these measurements, it is necessary to increase the accuracy of the sensor displacement measurement. This invention describes a way to solve this issue.

Figure 2:
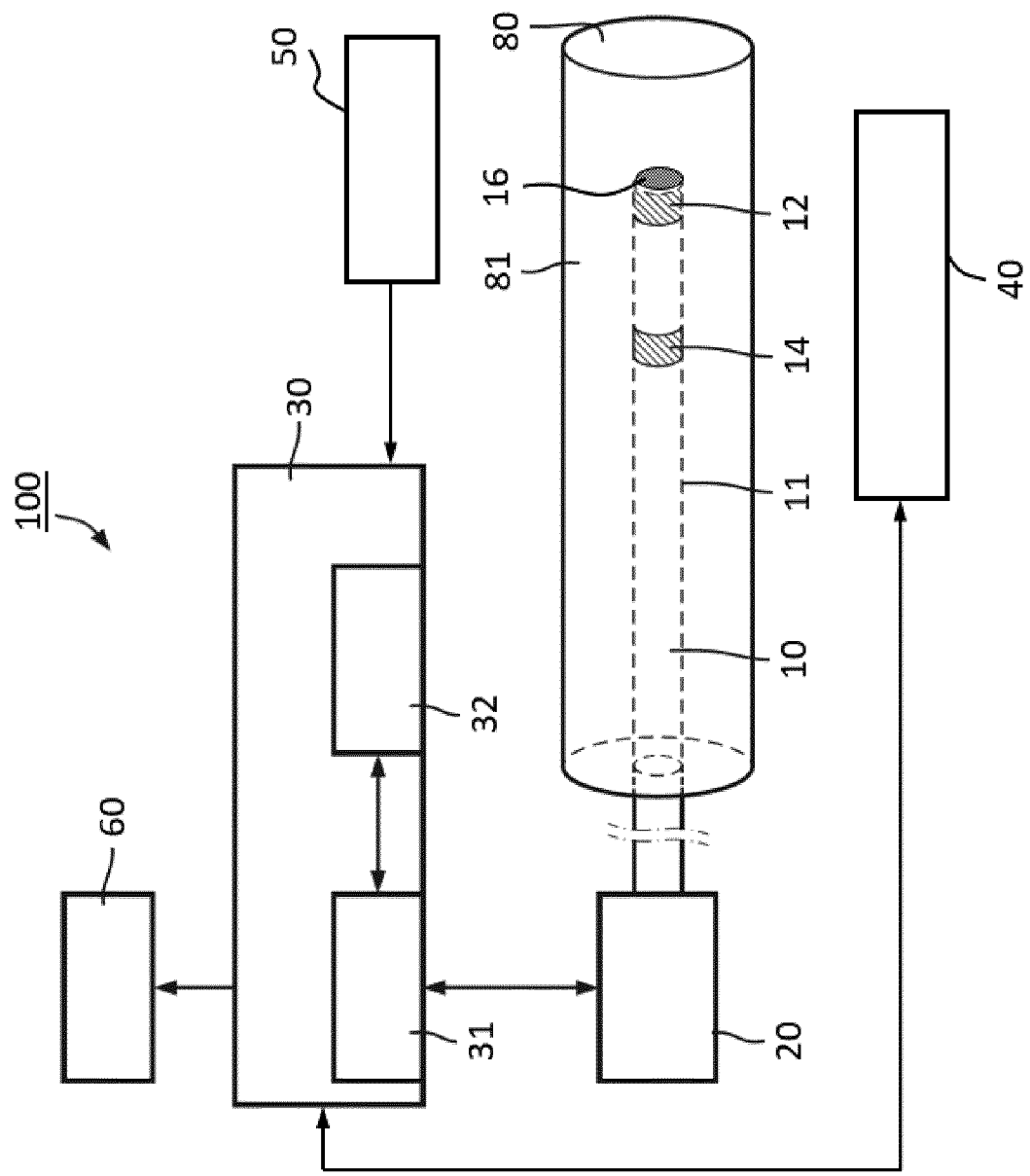
FIG. 2 illustrates schematically and exemplarily the general concept of the system according to the invention.

For the general concept, a schematic and exemplary system 100 is illustrated in FIG. 2, wherein for various advantageous embodiments of the system the functionality of an element may be fulfilled by various different devices or sub-systems, as it will be elucidated in the description. The system 100, which may be referred to as pulse wave velocity measurement system, may be used for patient stratification for treatment purposes. For example, the PWV value in the renal arteries may be utilized to determine whether a patient is suitable for renal artery denervation. Based on the PWV determination, the intravascular system 100 may be used to classify one or more patients into groups respectively associated with varying degrees of predicted therapeutic benefit of renal denervation. Any suitable number of groups or categories are contemplated. For example, the groups may include groups respectively for those patients with low, moderate, and/or high likelihood of therapeutic benefit from renal denervation, based on the PWV. Based on the stratification or classification, the system 100 can recommend the degree to which one or more patients are eligible candidates for renal denervation.

The vessel 80 may represent fluid-filled structures, both natural and artificial ones. The vessel 80 may be within a body of a patient. Walls of the vessel 80 define a lumen 81 through which fluid flows within the vessel 80. The vessel 80 may be a blood vessel, as an artery or a vein of a patient's vascular system, including cardiac vasculature, peripheral vasculature, cerebral vasculature, renal vasculature, and/or or any other suitable lumen inside the body. For example, the intravascular device 10 may be used to examine any number of anatomical locations in vessels of organs including the liver, heart, kidneys, gall bladder, pancreas, lungs, intestines, brain, urinary tract. In addition to natural structures, the intravascular device 10 may be used to examine artificial structures such as, but without limitation, grafts, stents, shunts.

The vessel 80 may be located within a body portion. When the vessel 80 is the renal artery, the patient body portion may include the abdomen, lumbar region, and/or thoracic region. In some examples, the vessel 80 may be located within any portion of the patient body, including the head, neck, chest, abdomen, arms, groin, legs, etc.

Figure 3:
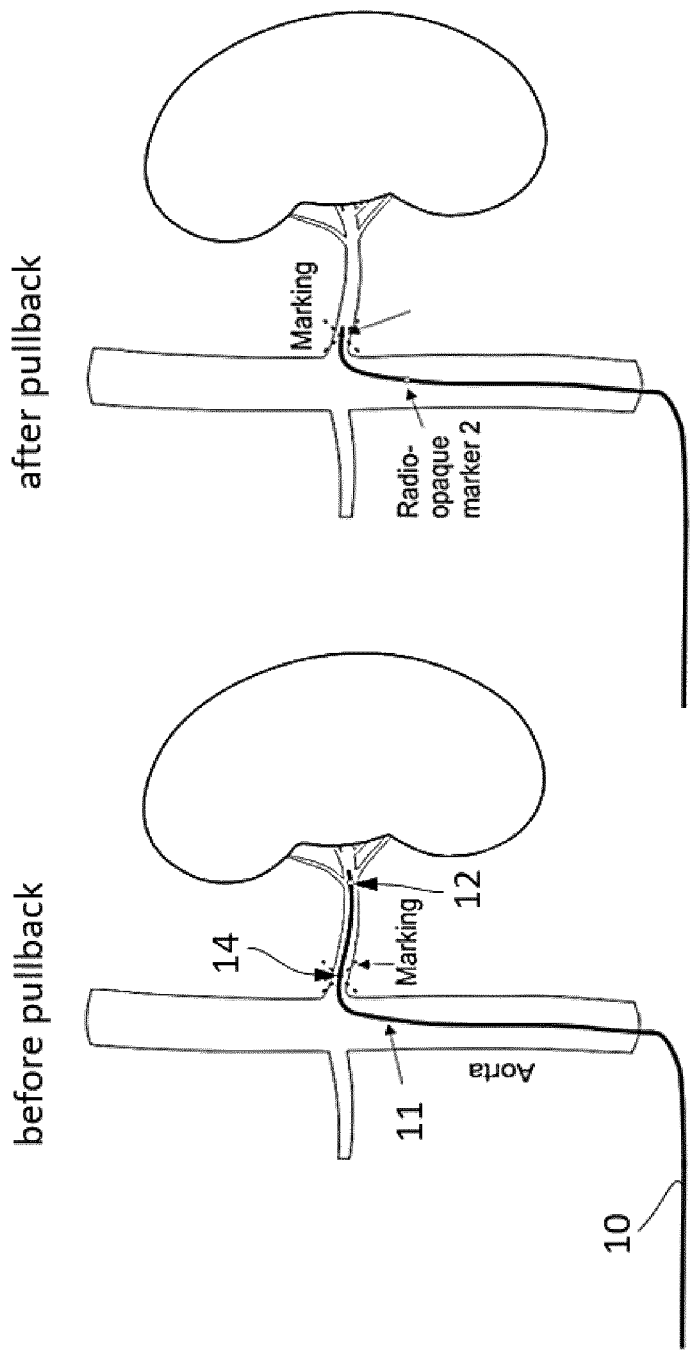
FIG. 3 shows schematically and exemplarily a measurement procedure according to the invention.
Figure 4:
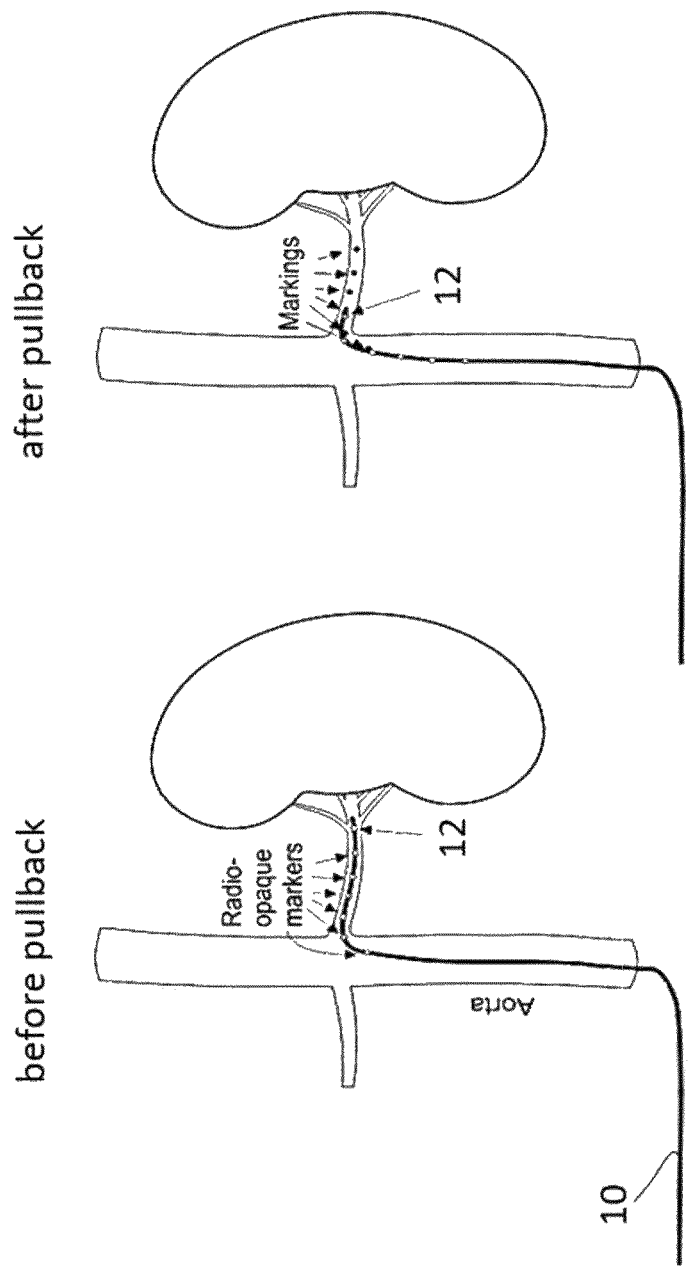
FIG. 4 shows schematically and exemplarily an alternative measurement procedure according to the invention.

The intravascular device 10 may include a flexible elongate member 11 such as a catheter, guide wire, or guide catheter, or other long, thin, long, flexible structure that may be inserted into a vessel 80 of a patient. The vessel 80 may be a renal artery as shown in FIGS. 3 and 4. The intravascular device 10 of the present disclosure has a cylindrical profile with a circular cross-section that defines an outer diameter of the intravascular device 10, in other instances, all or a portion of the intravascular device may have other geometrical cross-sectional profiles (e.g., oval, rectangular, square, elliptical, etc.). The intravascular device 10 may or may not include a lumen extending along all or a portion of its length for receiving and/or guiding other instruments. If the intravascular device 10 includes a lumen, the lumen may be centered or offset with respect to the cross-sectional profile of the intravascular device 10.

The intravascular device 10, or the various components thereof, may be manufactured from a variety of materials, including, by way of non-limiting example, plastics, polytetrafluoroethylene (PTFE), polyether block amide (PEBAX), thermoplastic, polyimide, silicone, elastomer, metals, such as stainless steel, titanium, shape-memory alloys such as Nitinol, and/or other biologically compatible materials. In addition, the intravascular device may be manufactured in a variety of lengths, diameters, dimensions, and shapes, including a catheter, guide wire, a combination of catheter and guide wire, etc. For example, the flexible elongate member 11 may be manufactured to have length ranging from approximately 115 cm-195 cm. The flexible elongate member 11 may be manufactured to have length of approximately 135 cm. The flexible elongate member 11 may be manufactured to have an outer transverse dimension or diameter ranging from about 0.35 mm-2.67 mm (1 Fr-8 Fr). The flexible elongate member 11 may be manufactured to have a transverse dimension of 2 mm (6 Fr) or less, thereby permitting the intravascular device 10 to be configured for insertion into the renal vasculature of a patient. These examples are provided for illustrative purposes only, and are not intended to be limiting. In some examples, the intravascular device is sized and shaped such that it can be moved inside the vasculature (or other internal lumen(s)) of a patient such that at least one of pressure, volumetric flow, flow velocity, vessel diameter and wall thickness of a vessel can be monitored from within and along a length of the vessel.

The intravascular device 10 includes a sensor 16 at the distal portion of the flexible elongate member 11. Alternatively or additionally, further sensors may be included along the length of the flexible elongate member. The intravascular device comprises two markers 12 and 14, provided at different locations along the flexible elongate member, and of which positions within the vessel 80 are localizable by a tracking apparatus 40. The system further comprises an external console, or apparatus 30, to receive the plurality of measurements provided by the intravascular device 10, to process the measurement signals by a processor 31, and optionally or alternatively to store the received measurement signals and/or processed measurement signals in a memory unit 32. The measurements provided by the intravascular device 10 may directly be transmitted to the external console 30, or alternatively they may be transmitted through a patient interface module 20 to which the intravascular device is connected. The patient interface module may transmit the measurement information to the external console either by wired or wireless connection. Optionally, the system comprises an electrocardiogram (ECG) unit 50 for measurement of internal electrogram or external electrocardiogram signals, which are transmitted to the apparatus 30 for using ECG signals, when required, for ascertaining pulse wave velocity value, in combination with the plurality of measurement signals received from the intravascular device 10. The internal electrogram signals may be measured by an electrode placed on an intravascular device that is introduced in a vessel, while the external electrocardiograms may be measured by external leads attached to the body of the patient.

In general, sensor 16 may provide one type of measurements or multiple types of measurements from the group of pressure measurements, flow measurements, vessel diameter measurements and vessel cross-section measurements. The multiple types of measurements with the same sensor may be performed simultaneously or interspersed. An example of such sensor is a capacitive micromachined sensor, which can emit and receive ultrasound waves, while from its design comprises a cavity closed by a membrane that upon pressure can vary capacitance value and hence can provide pressure measurements. Alternatively, the pressure value can be determined from the frequency characteristics at which the ultrasound emission and/or reception occurs, which are pressure sensitive. Once the capacitive micromachined sensor is operated to emit and receive ultrasound waves, ultrasound imaging of the vessel can be performed, and flow velocity can be measured by using ultrasound-Doppler principle. Vessel diameter and/or vessel cross-section can be determined from the ultrasound image, and having additionally the flow velocity of blood in the vessel, the volumetric flow can be calculated.

In the specific embodiment, schematically illustrated in FIG. 3, the system comprises an intravascular guidewire with a single pressure sensor at or near the distal tip. In the proximity of the pressure sensor a first radiopaque marker is placed. A second radiopaque marker is placed proximally to the first marker, at a fixed distance $\Delta x$, with $\Delta x$ in the range of 0.5 cm to 4 cm for an intravascular device configured for measurements in the renal arteries. The system further comprises the apparatus 30 to read out the pressure pulses and to derive a pulse delay time $\Delta T$ using ECG signal or alternatively, stationary pressure or flow sensor signal as a reference. The system further comprises a radiology (x-ray) system or apparatus suitable for angiographic imaging with functionality of the above mentioned tracking apparatus 40, and which additionally may provide morphological information (image) of the vessel anatomy. Alternatively, computer tomography (CT) or magnetic resonance imaging (MRI) may be used for acquiring three-dimensional morphological information (anatomy of the vessel) while tracking the markers. For MRI tracking coils integrated in the intravascular device may be used.

To measure pulse wave velocity, the physician places the intravascular device into the blood vessel under investigation so that the angiogram shows both radiopaque markers inside the blood vessel. Because the guidewire between the two markers is sufficiently stiff, the distance between both markers is known with a high degree of precision: which is $\Delta x$. The position of the second marker on the radiologic or angiographic image is recorded or labeled with a marking, either automatically by the system or manually by the physician. The physician will then measure the pulse delay time $\Delta T_1$ at this position, typically by averaging over multiple heartbeats. After this first measurement, the physician then gently pulls back the intravascular device until the new position of the first radiopaque marker on the image coincides with the marking showing the old position of the second radiopaque marker. This indicates a displacement of the sensor 16 by distance $\Delta x$ from the first measurement location. The physician will now measure the pulse delay time $\Delta T_2$ at this new position, averaging over the same number of heartbeats as before.

The processor will then calculate and optionally display PWV as:

$$PWV = \frac{\Delta T_1 - \Delta T_2}{\Delta x} \qquad \text{Eq. 2}$$

The second embodiment of the system, illustrated in FIG. 4, is similar to the first embodiment, except that the guidewire/catheter tip comprises multiple radiopaque markers proximally from the sensor at fixed, known distances from each other. Because the guidewire between the markers is sufficiently stiff, these markers form a kind of ruler that is visible under radiologic and/or angiographic imaging.

To measure pulse wave velocity, the physician places the intravascular device into the blood vessel under investigation, so that the pressure sensor is located as distally as practicable. The physician will then measure the pulse delay time $\Delta T_1$ at this position, typically by averaging over multiple heartbeats. During the measurement, the position of the radiopaque markers on the radiologic or angiographic image is recorded automatically and the distances between markers on the image are compared with the true distances of the markers. The ratio of apparent distances and true (or physical) distances provides a local correction factor for the processing unit that corrects for the local angle between the intravascular device and its projection on the radiologic or angiographic image, which is caused due to bending of the vessel or the shaft. After the first measurement, the physician then gently pulls back the intravascular device towards the proximal portion of the vessel under investigation. The sensor still has to be within the part of the vessel previously covered by the radiopaque markers. The physician will now measure the pulse delay time $\Delta T_2$ at this new position, averaging over the same number of heartbeats as before. During the measurement, the position of the radiopaque markers on the angiogram is again recorded automatically and the new locations of the radiopaque markers are compared with their old positions. Using the correction factors derived for the first measurement, the processing unit uses this information to calculate a corrected distance $\Delta x$ between the positions of the sensor at the first and second measurement instances.
The system will then calculate and display PWV according to Eq. 2.

The third embodiment of the system is either one of the first and second embodiments of the system, wherein the radiology apparatus is replaced with an ultrasound imaging system and the radiopaque markers are replaced by markers that are visible under ultrasound imaging.

In a forth embodiment of the system, which is a further alternative of the third embodiment, the markers are active or passive ultrasound transducers that emit or receive, respectively, ultrasound waves to or from an ultrasound probe, which can be a further ultrasound device configured to be introduced into the body of the subject or an extracorporeal ultrasound probe, wherein the locations of the active or passive ultrasound markers are tracked on the ultrasound image provided by the further ultrasound device or the extracorporeal ultrasound probe.

In a fifth embodiment of the system, which is a further alternative of the fourth embodiment of the system, the sensor is an ultrasound flow sensor and is simultaneously used as active ultrasound location marker.

In a sixth embodiment of the system, which may be based on the first or second embodiments of the system, the radiology apparatus is replaced with an electro-magnetic tracking system and the radiopaque markers are replaced by electromagnetic coils that are traceable with the electromagnetic tracking system.

In a seventh embodiment of the system, which may be based on any of the first to the sixth embodiments of the system, the location of the markers is continuously tracked during the measurements to correct for movement during the measurement such as breathing movement or patient movement.

In an eighth embodiment of the system, which may be based on any of the first to the seventh embodiments of the system, the system uses a vessel diameter measurement sensor like an intravascular ultrasound (IVUS) sensor instead of a pressure or flow sensor.

In a ninth embodiment, which is based on the eighth embodiment of the system, the IVUS sensor is used simultaneously as active ultrasound location marker.

In any of the relevant embodiments the system can be configured to ascertain the pulse wave velocity value of the vessel based on the plurality of measurements along the length of the vessel acquired as described above, wherein the plurality of measurements may alternatively be any of the combinations: pressure and vessel diameter measurements, pressure and flow velocity measurements, pressure and volumetric flow measurements, flow velocity and vessel diameter measurements, pressure and vessel wall thickness measurements. Reference is made to WO 2017/198800 A1, WO 2017/198867 A1, WO 2017/198490 A1, WO 2017/198871 A1, for description of using specific measurement combinations for calculation of pulse wave velocity.

For any of the embodiments where a morphology of the vessel is available besides the position of the markers within the vessel, the accuracy of the PWV calculation can further be improved by making the apparent distance $\Delta x$ in Eq. 1 or Eq. 2 for PWV measurements, be the distance from the first marker to the second marker projected on the axis of the vessel. For small distances, the apparent distance between the markers (which is needed for PWV measurements) can be different from the physical distance if the markers are not in the same radial position with respect to the axis of the vessel. This is an additional benefit compared to dual sensor measurements.

Figure 5:
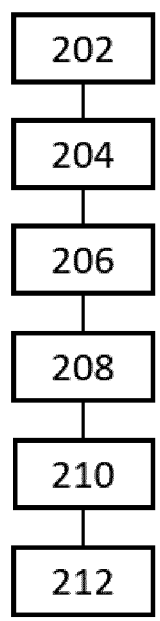
FIG. 5 shows schematically the functional use of the system according to the invention.

FIG. 5 illustrates schematically the functional use of any of the embodiments of the above systems according to the invention. The method 200 of measurement of pulse wave velocity of a vessel starts with step 202 of receiving plurality of measurements along the length of the vessel from an intravascular device. As already described for the systems, the intravascular device comprises at least two markers provided at different locations along the length of the intravascular device of which positions are localizable by the tracking apparatus. In step 204 the system receives position information of the two markers from the tracking apparatus and the system associates in step 206 for a first time a measurement of the plurality of measurements with the positions of the markers, wherein the first marker is in a first position and the second marker is in a second position. In step 208 the system detects, upon movement of the intravascular device within the vessel, from the position information when the first marker is reaching the second position and then associating a second time. In step 210 the pulse wave velocity value of the vessel is ascertained based on measurements associated for the first time and the second time from the plurality of measurements and based on the distance between the locations of the two markers along the length of the intravascular device.

In step 212 the pulse wave velocity value is output to a display. Alternatively or additionally, the pulse wave velocity value may be compared automatically by the processor to a threshold value for determining whether the patient is eligible for treatment or not, and the indication of eligibility is output to the display. Clinical studies provided evidence that any value of the pulse wave velocity for renal arteries above a threshold of about 9 m/s would make the patient eligible for renal denervation treatment with sufficient benefit in blood pressure reduction.

By repeating the steps 202 to 212 for successive portions of the vessel, a PWV map along the vessel can be generated and displayed as overlay on, or adjacent to, the morphological information of the vessel, which may be a two- or three-dimensional image of the vessel acquired by angiography or other imaging modality, such as for example ultrasound imaging. The eligibility of the patient for renal denervation treatment with sufficient benefit in blood pressure reduction can then be assessed based on a more comprehensive set of information provided by the PWV map along the vessel.

Although the invention is primarily described exemplarily for measurement of pulse wave velocity in renal arteries, it is applicable for measurement of pulse wave velocity in any other vessel, including cardiovascular and cerebral vessels.

Other variations to the disclosed embodiments can be understood and effected by those skilled in the art in practicing the claimed invention, from a study of the drawings, the disclosure, and the appended claims.

A single unit or device may fulfill the functions of several items recited in the claims. The mere fact that certain measures are recited in mutually different dependent claims does not indicate that a combination of these measures cannot be used to advantage.

In the claims, the word "comprising" does not exclude other elements or steps, and the indefinite article "a" or "an" does not exclude a plurality.

Any reference signs in the claims should not be construed as limiting the scope.

The invention claimed is:

1. A system for measurement of pulse wave velocity of a vessel, comprising:
    an intravascular device configured to provide plurality of measurements along the length of the vessel, wherein the intravascular device comprises two markers provided at different locations along the length of the intravascular device of which positions are localizable by a tracking apparatus;
    an apparatus configured to:
        receive the plurality of measurements from the intravascular device;
        receive position information of the two markers from the tracking apparatus;
        associate for a first time a measurement of the plurality of measurements with the positions of the markers, wherein the first marker is in a first position and the second marker is in a second position;
        detect upon movement of the intravascular device from the position information when the first marker reaches the second position and associate a second time;
        ascertain the pulse wave velocity value of the vessel based on measurements associated for the first time and the second time from the plurality of measurements and based on the distance between the locations of the two markers along the length of the intravascular device.

2. The system according to claim 1, wherein the intravascular device comprises a sensor at its distal portion, in proximity of one of the two markers, configured to provide the plurality of measurements along the length of the vessel.

3. The system of claim 1, wherein the apparatus is further configured to:
    ascertain an apparent distance between the first marker and the second marker at the first time from the position information received from the tracking apparatus;
    compare the apparent distance with the physical distance between the locations of the markers on the intravascular device;
    ascertain a local correction factor based on the apparent distance and the physical distance;
    ascertain a corrected pulse wave velocity value based on the pulse wave velocity value and the correction factor.

4. The system of claim 1, wherein the intravascular device comprises a plurality of markers localizable by the tracking apparatus and provided at different locations along the length of the intravascular device, wherein the plurality of markers form a ruler.

5. The system of claim 1, further comprising a user interface configured to display the pulse wave velocity value.

6. The system of claim 1, further comprising the tracking apparatus configured to localize the positions of the markers.

7. The system of claim 6, wherein the tracking apparatus is a radiology apparatus and the markers comprise radiopaque material.

8. The system of claim 1, wherein the plurality of measurements along the length of the vessel comprise at least one of the types of pressure measurements, flow measurements, vessel diameter measurements and vessel cross-section measurements.

9. The system of claim 6, wherein the tracking apparatus is an ultrasound probe and wherein the markers are active or passive ultrasound transducers that emit or receive, respectively, ultrasound waves to or from the ultrasound probe.

10. The system of claim 9, wherein the ultrasound probe is an extracorporeal ultrasound probe.

11. The system of claim 9, wherein at least one of the marker is used as the sensor to provide the plurality of measurements along the length of the vessel.

12. The system of claim 11, wherein the sensor is configured to provide the plurality of measurements comprising flow measurements.

13. The system of claim 11, wherein the sensor is configured to provide the plurality of measurements comprising vessel diameter or cross-section measurements.

14. The system of claim 6, wherein the tracking apparatus is electromagnetic tracking apparatus and wherein the markers comprise permanent magnetic material or electromagnetic coils.

15. A method of measurement of pulse wave velocity of a vessel, comprising:
    receiving plurality of measurements along the length of the vessel from an intravascular device, the intravascular device comprising two markers provided at different locations along the length of the intravascular device of which positions are localizable by a tracking apparatus;
    receiving position information of the two markers from the tracking apparatus;
    associating for a first time a measurement of the plurality of measurements with the positions of the markers, wherein the first marker is in a first position and the second marker is in a second position;
    detecting upon movement of the intravascular device from the position information when the first marker reaches the second position and associating a second time;
    ascertaining the pulse wave velocity value of the vessel based on measurements associated for the first time and the second time from the plurality of measurements and based on the distance between the locations of the two markers along the length of the intravascular device.

* * * * *